(12) United States Patent
Jakob-Roetne et al.

(10) Patent No.: US 8,227,461 B2
(45) Date of Patent: Jul. 24, 2012

(54) ISOXAZOLES

(75) Inventors: Roland Jakob-Roetne, Inzlingen (DE); Matthew C. Lucas, Verona, NJ (US); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 8 days.

(21) Appl. No.: 12/766,202

(22) Filed: Apr. 23, 2010

(65) Prior Publication Data
US 2010/0280020 A1 Nov. 4, 2010

(30) Foreign Application Priority Data

Apr. 30, 2009 (EP) ..................... 09159150

(51) Int. Cl.
*A61K 31/541* (2006.01)
*A61K 31/5377* (2006.01)
*A61K 31/4439* (2006.01)
*C07D 417/14* (2006.01)
*C07D 413/14* (2006.01)
*C07D 401/12* (2006.01)

(52) U.S. Cl. .................. 514/227.8; 514/236.8; 514/340; 544/58.2; 544/124; 546/272.1

(58) Field of Classification Search ............... 514/227.8, 514/236.8, 340; 544/58.2, 124; 546/272.1
See application file for complete search history.

(56) References Cited

U.S. PATENT DOCUMENTS

| | | | |
|---|---|---|---|
| 4,639,266 A | 1/1987 | Heubach et al. | |
| 2003/0055085 A1 | 3/2003 | Wagener et al. | |
| 2004/0006226 A1 | 1/2004 | Ladduwahetty et al. | |
| 2009/0143371 A1* | 6/2009 | Buettelmann et al. ..... | 514/227.8 |

FOREIGN PATENT DOCUMENTS

| | | |
|---|---|---|
| DE | 3525205 | 3/1986 |
| GB | 2336589 | 10/1999 |
| JP | 2007230909 | 9/2007 |
| WO | 0129015 | 4/2001 |
| WO | 200134603 | 5/2001 |
| WO | 0250062 | 6/2002 |
| WO | 02081474 | 10/2002 |
| WO | 03004027 | 1/2003 |
| WO | 03015771 | 2/2003 |
| WO | 2003044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007039389 | 4/2007 |
| WO | 2007052843 | 5/2007 |
| WO | 2007076260 | 7/2007 |
| WO | 2007092751 | 8/2007 |
| WO | 2008025539 | 3/2008 |
| WO | 2008025540 | 3/2008 |
| WO | 2009/071476 | 6/2009 |

OTHER PUBLICATIONS

International Search Report by EPO for case 25375, International Appl. PCT/EP2010/055591, mailed Jul. 23, 2010.
McNamara et al., Psychobiology (1993), vol. 21, pp. 101-108.
Goodman et al., Tetrahedron (1999) vol. 55 pp. 15067-15070.
Abstract corresponding to JP 2007/230909, 2007.
Roy et al., Synthesis, 2003 pp. 1347-1356.
White, et al., Journal of Organic Chemistry (1981), vol. 46(11) pp. 2273-2280.
Shi Shun et al., J Org. Chem. vol. 68 (2003) pp. 6810-6813.
Lam et al., Bioorganic; & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.

(Continued)

*Primary Examiner* — Kamal Saeed
*Assistant Examiner* — Kristin Bianchi
(74) *Attorney, Agent, or Firm* — George W. Johnston; Patricia S. Rocha-Tramaloni; Kimberly J. Prior

(57) ABSTRACT

The present invention is concerned with novel isoxazole derivatives of formula I

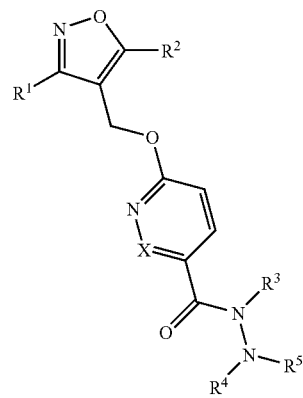

wherein X, $R^1$, $R^2$, $R^3$, $R^4$ and $R^5$ are as described herein, as well as pharmaceutically acceptable salts and esters thereof. The active compounds of the present invention have affinity and selectivity for GABA A α5 receptor. Further the present invention is concerned with the manufacture of the active compounds of formula I, pharmaceutical compositions containing them and their use as pharmaceuticals.

18 Claims, No Drawings

OTHER PUBLICATIONS

Kumar, et al. Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
DeLong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.

* cited by examiner

ISOXAZOLES

PRIORITY TO RELATED APPLICATION(S)

This application claims the benefit of European Patent Application No. 09159150.3, filed Apr. 30, 2009, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

The present invention provides isoxazoles having affinity and selectivity for GABA A α5 receptor, their manufacture, pharmaceutical compositions containing them and their use as pharmaceuticals.

In particular, the present invention provides isoxazoles of formula I

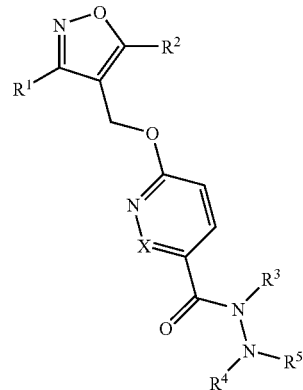

X is $CR^6$ or N, wherein $R^6$ is hydrogen or lower-alkyl;

$R^1$ is lower-alkyl, aryl or heteroaryl,
  wherein lower-alkyl is optionally substituted with 1-4 substituents independently selected from the group consisting of halogen, cyano, hydroxy and lower-alkoxy, and wherein aryl and heteroaryl are each optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H,lower-alkyl), lower-alkyl-CO—N(lower-alkyl)$_2$, lower-alkyl-$NH_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$—$NH_2$, $SO_2$—N(H,lower-alkyl) and $SO_2$—N(lower-alkyl)$_2$;

$R^2$ is hydrogen or lower-alkyl which is optionally substituted with 1-4 substituents independently selected from the group consisting of halogen, cyano, lower-alkyl and lower-alkoxy;

$R^3$ is hydrogen or lower-alkyl which is optionally substituted with 1-4 substituents independently selected from the group consisting of halogen, cyano, hydroxy, lower-alkyl and lower-alkoxy;

$R^4$ and $R^5$ are each independently selected from the group consisting of hydrogen, lower-alkyl, $SO_2$-lower-alkyl, cycloalkyl and heterocyclyl, optionally substituted with 1-4 substituents independently selected from the group consisting of halogen, cyano, hydroxy, lower-alkyl and lower-alkoxy, or wherein $R^4$ and $R^5$, together with the nitrogen atom to which they are attached, form a heterocyclyl, optionally substituted with 1-4 substituents independently selected from the group consisting of halogen, cyano, hydroxy, oxo, lower-alkyl and lower-alkoxy;

and pharmaceutically acceptable salts and esters thereof.

In particular, the present invention provides compounds of formula I and their pharmaceutically acceptable salts and esters and pharmaceutical compositions containing them. The invention also provides methods for the manufacture of the compounds and compositions of the invention. The invention further provides methods for the treatment or prevention of diseases related to the GABA A α5 receptor.

The compounds of present invention are preferably inverse agonists of GABA A α5. The compounds of present invention and their pharmaceutically acceptable salts and esters can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

DETAILED DESCRIPTION OF THE INVENTION

Unless otherwise indicated, the following definitions are set forth to illustrate and define the meaning and scope of the various terms used to describe the invention herein. The following definitions of the general terms apply irrespective of whether the terms in question appear alone or in combination.

The nomenclature used in this application is based on AutoNom™ 2000, a Beilstein Institute computerized system for the generation of IUPAC systematic nomenclature. Chemical structures shown herein were prepared using ISIS™/Draw version 2.5. Any open valency appearing on a carbon, oxygen, sulfur or nitrogen atom in the structures herein indicates the presence of a hydrogen atom.

The term "substituted", unless specifically defined otherwise, means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. 1, 2, 3, 4 or 5 substituents are preferred, unless specifically defined otherwise.

The term "halogen" refers to fluorine, chlorine, bromine and iodine, with fluorine being preferred.

The term "lower-alkyl" denotes a saturated straight- or branched-chain group containing from 1 to 7 carbon atoms, for example, methyl, ethyl, propyl, isopropyl, n-butyl, isobutyl, sec-butyl or tert-butyl, as well as those groups specifically illustrated by the examples herein below. Preferred lower-alkyl groups are methyl and n-butyl.

The term "lower-alkoxy" denotes a group —O—R wherein R is lower-alkyl as defined above.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl or cyclohexyl, as well as those groups specifically illustrated by the examples herein below.

The term "heterocyclyl" refers to a monovalent 3 to 7 membered saturated or partly unsaturated monocyclic ring containing one, two or three ring heteroatoms selected from N, O and S. One or two ring heteroatoms are preferred. Preferred are 4 to 6 membered heterocyclyl comprising one or two ring heteroatoms selected from N, O and S. S is optionally substituted by two oxo groups. Examples for heterocyclyl moieties are pyrrolidinyl, tetrahydro-furanyl, tetrahydro-pyranyl, tetrahydro-thienyl, tetrahydro-pyridinyl, tetrahydropyryl, azetidinyl, thiazolidinyl, oxazolidinyl, piperidinyl, morpholinyl, thiomorpholinyl, 1,1-dioxo-thiomorpholin-4-yl, piperazinyl, azepanyl, diazepanyl, oxazepanyl and dihydro-oxazolyl, as well as those groups specifically illustrated by the examples herein below. Among the preferred heterocyclyls are morpholin-4-yl, piperidin-1-yl, pyrrolidin-1-yl, thiomorpholin-4-yl and 1,1-dioxo-thiomorpholin-4-yl. Particularly preferred heterocyclyls are morpholin-4-yl, pyrrolidin-1-yl and 1,1-dioxo-thiomorpholin-4-yl.

The term "aryl" refers to a monovalent aromatic carbocyclic ring system, comprising 6 to 14, preferably 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g. as defined below and in the claims.

The term "heteroaryl" refers to an aromatic 5 to 6 membered monocyclic ring or 9 to 10 membered bicyclic ring which comprises 1, 2 or 3 heteroatoms selected from nitrogen, oxygen and sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl or isoquinolinyl, as well as those groups specifically illustrated by the examples herein below. Heteroaryl can also be substituted e.g. as defined below and in the claims. Preferred heteroaryl group is 5-fluoro-pyridin-2-yl.

The term "lower-alkyl substituted by halogen" refers to lower-alkyl groups which are mono- or multiply substituted with halogen. Examples of lower-alkyl substituted by halogen groups are e.g. $CFH_2$, $CF_2H$, $CF_3$, $CF_3CH_2$, $CF_3(CH_2)_2$, $(CF_3)_2CH$ or $CF_2H—CF_2$, as well as those groups specifically illustrated by the examples herein below.

The term "lower-alkyl substituted by hydroxy" denotes a lower-alkyl group as defined above wherein at least one of the hydrogen atoms of the alkyl group is replaced by a hydroxy group. Examples of lower-alkyl substituted by hydroxy include but are not limited to methyl, ethyl, propyl, isopropyl, isobutyl, sec-butyl, tert-butyl, pentyl and n-hexyl substituted by one or more hydroxy group(s), in particular with one, two or three hydroxy groups, preferably with one or two hydroxy groups.

"Pharmaceutically acceptable," such as pharmaceutically acceptable carrier, excipient, etc., means pharmacologically acceptable and substantially non-toxic to the subject to which the particular compound is administered.

Compounds of formula I can form pharmaceutically acceptable acid addition salts. Examples of such pharmaceutically acceptable salts are salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

The term "pharmaceutically acceptable esters" embraces derivatives of the compounds of formula I, in which a carboxy group has been converted to an ester. Lower-alkyl, lower-alkyl substituted by hydroxy, lower-alkyl substituted by lower-alkoxy, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aryl-lower-alkyl esters are examples of suitable esters. The methyl, ethyl, propyl, butyl and benzyl esters are preferred esters. The term "pharmaceutically acceptable esters" furthermore embraces compounds of formula I in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention provides compounds of formula I

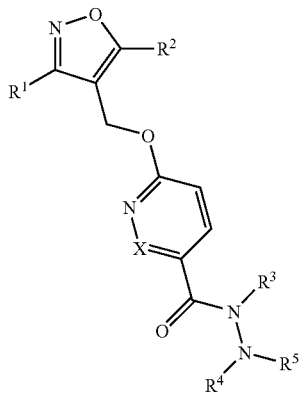

I wherein
X is $CR^6$ or N, wherein $R^6$ is hydrogen or lower-alkyl;
$R^1$ is lower-alkyl, aryl or heteroaryl,
    wherein lower-alkyl is optionally substituted with 1-4 substituents independently selected from the group consisting of halogen, cyano, hydroxy and lower-alkoxy, and wherein aryl and heteroaryl are each optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H,lower-alkyl), lower-alkyl-CO—N(lower-alkyl)$_2$, lower-alkyl-$NH_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$—$NH_2$, $SO_2$—N(H,lower-alkyl) and $SO_2$—N(lower-alkyl)$_2$;

$R^2$ is hydrogen or lower-alkyl which is optionally substituted with 1-4 substituents independently selected from the group consisting of halogen, cyano, lower-alkyl and lower-alkoxy;

$R^3$ is hydrogen or lower-alkyl which is optionally substituted with 1-4 substituents independently selected from the group consisting of halogen, cyano, hydroxy, lower-alkyl and lower-alkoxy;

$R^4$, $R^5$ are independently from each other selected from the group consisting of hydrogen, lower-alkyl, $SO_2$-lower-alkyl, cycloalkyl and heterocyclyl, optionally substituted with 1-4 substituents independently selected from the group consisting of halogen, cyano, hydroxy, lower-alkyl and lower-alkoxy, or wherein $R^4$ and $R^5$, together with the nitrogen atom to which they are attached, form a heterocyclyl, optionally substituted with 1-4 substituents independently selected from the group consisting of halogen, cyano, hydroxy, oxo, lower-alkyl and lower-alkoxy;

and pharmaceutically acceptable salts and esters thereof.

Compounds of formula I are individually preferred and pharmaceutically acceptable salts thereof are individually preferred and pharmaceutically acceptable esters thereof are individually preferred, with the compounds of formula I being particularly preferred.

The compounds of formula I can have one or more asymmetric carbon atom and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemate, by asymmetric synthesis or asymmetric chromatography (chromatography with a chiral adsorbens or eluant). The invention embraces all of these forms.

Further, it is to be understood that every embodiment relating to a specific residue $R^1$ to $R^5$ as disclosed herein can be combined with any other embodiment relating to another residue $R^1$ to $R^5$ as disclosed herein.

In certain embodiments, the present invention provides compounds of formula I wherein
X is CH or N;
$R^1$ is lower-alkyl, aryl or heteroaryl,
    wherein lower-alkyl is optionally substituted with 1-4 substituents independently selected from the group consisting of halogen, cyano, hydroxy and lower-alkoxy,
    and wherein aryl and heteroaryl are each optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H, lower-alkyl), lower-alkyl-CO—N(lower-alkyl)$_2$, lower-alkyl-$NH_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$—$NH_2$, $SO_2$—N(H,lower-alkyl) and $SO_2$—N(lower-alkyl)$_2$;

$R^2$ is hydrogen or lower-alkyl which is optionally substituted with 1-4 substituents independently selected from the group consisting of halogen, cyano, lower-alkyl and lower-alkoxy;

$R^3$ is hydrogen or lower-alkyl which is optionally substituted with 1-4 substituents independently selected from the group consisting of halogen, cyano, hydroxy, lower-alkyl and lower-alkoxy;

$R^4$ and $R^5$ are each independently selected from the group consisting of hydrogen, lower-alkyl, $SO_2$-lower-alkyl, cycloalkyl and heterocyclyl, optionally substituted with 1-4 substituents independently selected from the group consisting of halogen, cyano, hydroxy, lower-alkyl and lower-alkoxy, or wherein $R^4$ and $R^5$, together with the nitrogen atom to which they are attached, form a heterocyclyl, optionally substituted with 1-4 substituents independently selected from the group consisting of halogen, cyano, hydroxy, lower-alkyl and lower-alkoxy;

and pharmaceutically acceptable salts and esters thereof.

In certain embodiments of the compound of formula I, X is CH or N, preferably CH.

In certain embodiments of the compound of formula I, $R^1$ is preferably lower-alkyl, aryl or heteroaryl substituted with halogen. Even more preferred compounds of the present invention are those, wherein $R^1$ is n-butyl, phenyl or 5-fluoro-pyridin-2-yl. Most preferred are compounds wherein $R^1$ is phenyl or 5-fluoro-pyridin-2-yl.

In certain embodiments of the compound of formula I, $R^2$ is lower-alkyl. Preferred compounds of the present invention are those, wherein $R^2$ is methyl.

In certain embodiments of the compound of formula I, $R^3$ is hydrogen or lower-alkyl. Preferred compounds of the present invention are those, wherein $R^3$ is hydrogen.

In certain embodiments of the compound of formula I, $R^4$ and $R^5$ are each independently selected from the group consisting of hydrogen, lower-alkyl and $SO_2$-lower-alkyl.

Preferred compounds of the present invention are those, wherein $R^4$ and $R^5$ are each independently selected from the group consisting of hydrogen, methyl and $SO_2$-methyl. Even more preferred are compounds wherein $R^4$ is hydrogen and $R^5$ is $SO_2$-methyl. Evenly preferred are embodiments wherein both $R^4$ and $R^5$ are identically either hydrogen or methyl.

In certain embodiments of the compound of formula I, $R^4$ and $R^5$, together with the nitrogen atom to which they are attached, form a heterocyclyl. Preferred compounds of the present invention are those, wherein $R^4$ and $R^5$, together with the nitrogen atom to which they are attached, form a heterocyclyl selected from the group consisting of morpholin-4-yl, piperidin-1-yl, pyrrolidin-1-yl and 1,1-dioxo-thiomorpholin-4-yl. Most preferred are compounds wherein $R^4$ and $R^5$, together with the nitrogen atom to which they are attached, form a heterocyclyl selected from the group consisting of morpholin-4-yl, pyrrolidin-1-yl and 1,1-dioxo-thiomorpholin-4-yl.

In particular, preferred compounds are the compounds of formula I described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Particularly preferred compounds of formula I of present invention are those selected from the group consisting of:

6-((5-Methyl-3-phenyl-isoxazol-4-yl)-methoxy)-nicotinic acid hydrazide,
6-((5-Methyl-3-phenyl-isoxazol-4-yl)-methoxy)-N-morpholin-4-yl-nicotinamide,
6-((5-Methyl-3-phenyl-isoxazol-4-yl)-methoxy)-N-piperidin-1-yl-nicotinamide,
6-((5-Methyl-3-phenyl-isoxazol-4-yl)-methoxy)-N-pyrrolidin-1-yl-nicotinamide,
N-(1,1-Dioxo-1,6-thiomorpholin-4-yl)-6-((5-methyl-3-phenyl-isoxazol-4-yl)-methoxy)-nicotinamide,
6-((5-Methyl-3-phenyl-isoxazol-4-yl)-methoxy)-nicotinic acid N'-(methyl sulfonyl)-hydrazide,
6-[((3-(5-Fluoro-pyridin-2-yl)-5-methyl-isoxazol-4-yl)-methoxy]-N-morpholin-4-yl-nicotinamide,
6-((3-Butyl-5-methyl-isoxazol-4-yl)-methoxy)-N-morpholin-4-yl-nicotinamide,
6-((3-Butyl-5-methyl-isoxazol-4-yl)-methoxy)-N-pyrrolidin-1-yl-nicotinamide,
6-((3-Butyl-5-methyl-isoxazol-4-yl)-methoxy)-nicotinic acid 2,2-dimethyl-hydrazide, and
6-((5-Methyl-3-phenyl-isoxazol-4-yl)-methoxy)-pyridazine-3-carboxylic acid morpholin-4-ylamide,
and pharmaceutically acceptable salts and esters thereof.

Even more preferred compounds of formula I of present invention are those selected from the group consisting of:

6-((5-Methyl-3-phenyl-isoxazol-4-yl)-methoxy)-N-morpholin-4-yl-nicotinamide,
6-((5-Methyl-3-phenyl-isoxazol-4-yl)-methoxy)-N-pyrrolidin-1-yl-nicotinamide,
N-(1,1-Dioxo-1,6-thiomorpholin-4-yl)-6-((5-methyl-3-phenyl-isoxazol-4-yl)-methoxy)-nicotinamide, and
6-[(3-(5-Fluoro-pyridin-2-yl)-5-methyl-isoxazol-4-yl)-methoxy]-N-morpholin-4-yl-nicotinamide, and pharmaceutically acceptable salts and esters thereof.

The invention further provides a process for the manufacture of compounds of formula I as defined above, which process comprises:

a) reacting a compound of formula II:

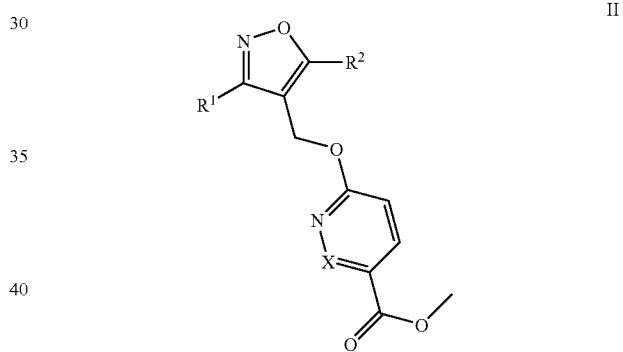

II with $HNR^3NR^4R^5$, or
b) reacting a compound of formula III:

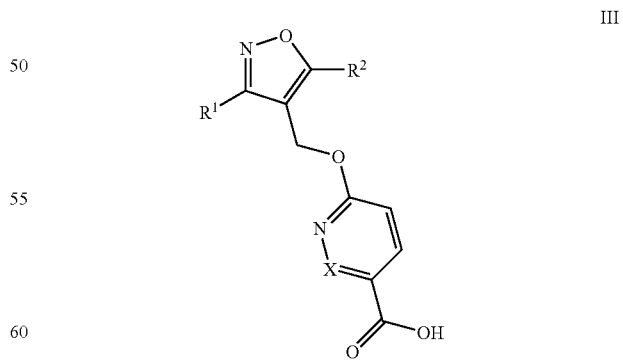

III with $HNR^3NR^4R^5$, or
c) saponification of a compound of formula II to obtain a compound of formula III followed by reaction with $HNR^3NR^4R^5$.

wherein $R^1$, $R^2$, $R^3$, $R^4$, $R^5$ and X are as defined above.

The reaction of a compound of formula II with HNR³NR⁴R⁵ to obtain a compound of formula I can be carried out under conditions as described in the examples or under conditions well known to the person skilled in the art. For example, the reaction can be performed in the presence of trimethylaluminium in a suitable solvent like dioxane at elevated temperatures e.g. at 85-95° C.

The reaction of a compound of formula III with HNR³NR⁴R⁵ to obtain a compound of formula I can be carried out under conditions as described in the examples or under conditions well known to the person skilled in the art. For example, the reaction can be performed in the presence of Hünigs Base (N,N-diisopropylethylamine) and O-(benzotriazol-1-yl)-N,N,N',N'-tetramethyluronium tetrafluoroborate in a suitable solvent like dimethylformamide at room temperature. Alternatively, the reaction can be performed in the presence of 1,1'-carbonyldiimidazole in a suitable solvent like dimethylformamide at elevated temperatures e.g. at 80° C. Furthermore, the reaction can be performed in the presence of 1-ethyl-3-(3-dimethylaminopropyl)carbodiimide hydrochloride, N1-hydroxybenzotriazole and Hünigs Base (N,N-diisopropylethylamine) in a suitable solvent like dichloromethane at room temperature.

The saponification of a compound of formula II to obtain a compound of formula III can be carried out under conditions as described in the examples or under conditions well known to the person skilled in the art. For example, the reaction can be performed in the presence of sodiumhydroxide in a suitable solvent like water at room temperature. Alternatively, the reaction can be performed in the presence of lithiumhydroxide in a suitable solvent like methanol, tetrahydrofuran or water at room temperature.

The present invention also provides compounds of formula I as defined above, when prepared by a process as described above.

The present compounds of formula I and their pharmaceutically acceptable salts can be prepared by a process comprising the steps of:

a) reacting a compound of formula 1:

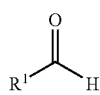

1 with hydroxylamine hydrochloride in a suitable solvent, such as ethanol and water in the presence of a base, such as aqueous sodium hydroxide to give a compound of formula 2:

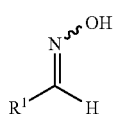

2 b) followed by reacting the compound of formula 2 with a chlorinating agent such as N-chlorosuccinimide in a suitable solvent, such as DMF to give a compound of formula 3:

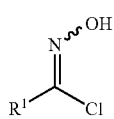

3 c) and then either reacting the compound of formula 3 with a compound of formula 4:

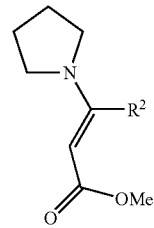

4 in the presence of a suitable base, such as triethylamine, in a suitable solvent, such as chloroform, to give a compound of formula 7:

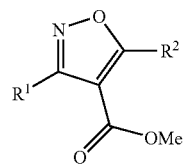

7 d) or alternatively reacting the compound of formula 3 with a compound of formula 5:

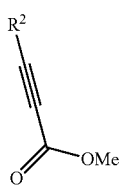

5 in the presence of a suitable base, such as triethylamine, in a suitable solvent, such as diethylether, to give a compound of formula 7;

e) or alternatively reacting the compound of formula 3 with a compound of formula 6:

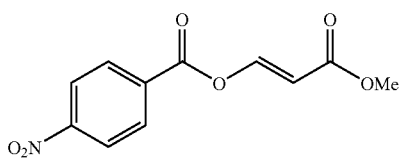

6 in the presence of a suitable base, such as triethylamine, in a suitable solvent, such as DCM, to give a compound of formula 7;

f) The compound of formula 7 can be reacted with a reducing agent, such as lithiumaluminiumhydride, in a suitable solvent, such as THF to give a compound of formula 8:

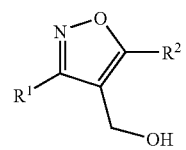

8 g) or alternatively a compound of formula 7 can be reacted with a hydrolytic agent such as NaOH or LiOH in a suitable solvent such as THF, MeOH or EtOH, water to give a compound of formula 9:

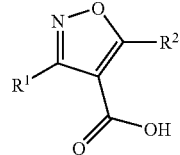

9 h) followed by reacting a compound of formula 9 with a reducing agent, such as lithiumaluminiumhydride or ethylchloroformate in the presence of sodiumborohydride in a suitable solvent such as THF or water to give a compound of formula 8;

i) Compounds of formula 8 can be reacted with a compound of formula 10:

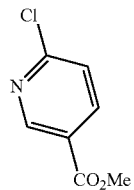

10 in the presence of a suitable base, such as sodium hydride, in a suitable solvent, such as THF to give a compound of formula II-A:

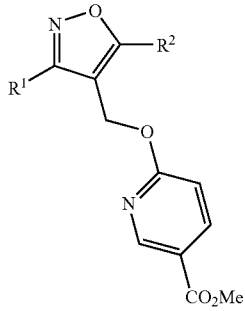

II-A j) Alternatively, a compound of formula 8 can be reacted with a compound of formula 11:

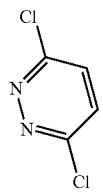

11 in the presence of a suitable base, such as sodium hydride, in a suitable solvent, such as THF, to give a compound of formula 12:

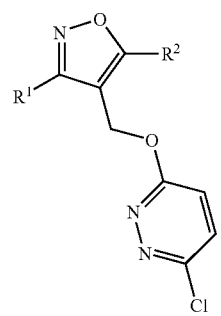

12 k) followed by reacting a compound of formula 12 with methanol in the presence of palladium(II) acetate and 1,1'-bis(diphenylphosphino)ferrocene as well as a suitable base such as sodium carbonate under a carbon monoxide atmosphere at elevated temperatures such as 50° C. to give a compound of formula II-B:

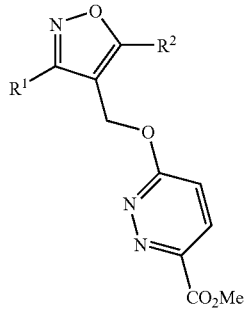

II-B

In accordance with Scheme 1, compounds of formula I can be prepared following standard methods.

Scheme 1

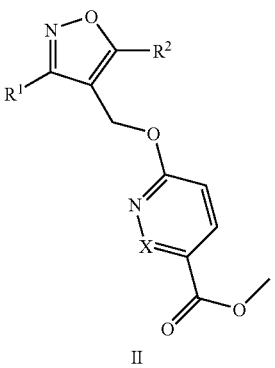 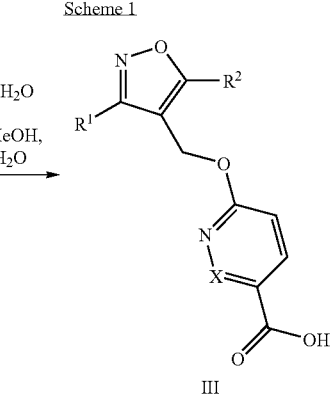

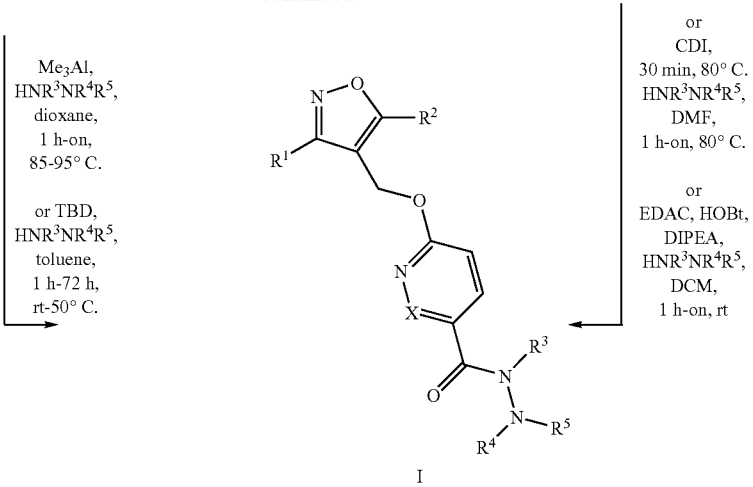

wherein $R^1$, $R^2$, $R^3$, $R^4$, $R^5$ and X are as defined above.
CDI=1,1'-carbonyldiimidazole
DCM=dichloromethane
DIPEA=N,N-diisopropylethylamine (Hünigs Base)
DMF=dimethylformamid
EDAC=1-ethyl-3-(3-dimethylaminopropyl)carbodiimide hydrochloride
HOBt=N1-hydroxybenzotriazole
$Me_3Al$=trimethylaluminium
on=overnight
rt=room temperature
TBD=1,5,7-triazabicyclo[4.4.0]dec-5-ene
TBTU=O-(benzotriazol-1-yl)-N,N,N',N'-tetramethyluronium tetrafluoroborate
THF=tetrahydrofuran The corresponding salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula I into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula I as well as all intermediate products can be prepared according to analogous methods or according to the methods set forth above. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

As described above, the novel compounds of the present invention and their pharmaceutically acceptable salts and esters possess valuable pharmacological properties and are ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another preferred embodiment, the invention relates to a method for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

The treatment or prevention of cognitive disorders, Alzheimer's disease, schizophrenia, positive, negative and/or cognitive symptoms associated with schizophrenia, Down syndrome, and neurofibromatosis type I, is preferred.

Particularly preferred is the treatment or prevention of Alzheimer's disease.

Particularly preferred is the treatment or prevention of Down syndrome.

Particularly preferred is the treatment or prevention of neurofibromatosis type I.

The compounds were investigated in accordance with the test given hereinafter:

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]-Flumazenil at a concentration of 1 nM for α1, α2, α3 subunits and 0.5 nM for α5 subunits and the test compound in the range of $10\text{-}10^{-3 \times 10^{-6}}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of [$^3$H]-Flumazenil from α5 subunits of the rat GABA A receptor of 100 nM or less. Most preferred are compounds with a $K_i$ (nM)<35. In a preferred embodiment the compounds of the invention are binding selective for the α5 subunit relative to the α1, α2 and α3 subunit.

Representative test results, obtained by the above described assay measuring binding affinity to HEK293 cells expressing human (h) receptors, are shown in table 1 below.

TABLE 1 binding affinities to HEK293 cells expressing human (h) receptors

| Example | $hK_i$ (GABA A$\alpha$5) |
|---|---|
| 1 | 5.4 |
| 2 | 0.6 |
| 3 | 4 |
| 4 | 2.6 |
| 5 | 2.6 |
| 6 | 4.8 |
| 7 | 0.4 |
| 8 | 6.4 |
| 9 | 19.4 |
| 10 | 18.7 |
| 11 | 9.5 |

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injection solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.1 to 1000 mg per person of a compound of formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

TABLE 2 possible tablet composition

| ingredient | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsules of the following composition are manufactured:

TABLE 3 possible capsule composition

| ingredient | mg/capsule |
|---|---|
| Active substance | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

TABLE 4 possible suppository composition

| ingredient | mg/supp. |
|---|---|
| Active substance | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1 to 11 are provided for illustration of the invention. They should not be considered as limiting the scope of the invention, but merely as being representative thereof.

EXAMPLE 1

6-((5-Methyl-3-phenyl-isoxazol-4-yl)-methoxy)-nicotinic acid hydrazide

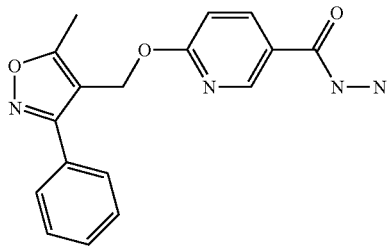

a) 6-(5-Methyl-3-phenyl-isoxazol-4-ylmethoxy)-nicotinic acid methyl ester

To a solution of (5-methyl-3-phenyl-isoxazol-4-yl)-methanol (263 mg, 1.39 mmol) in THF (3 mL) was added sodium hydride (55% dispersion in mineral oil, 66.7 mg, 1.53 mmol). After stirring for 15 min at room temperature methyl 6-chloronicotinate (286 mg, 1.67 mmol) was added and the reaction mixture was stirred for 18 h. The mixture was then diluted with ethyl acetate (10 mL), washed with aqueous citric acid (10%, 10 mL), water (10 mL) and aqueous sodium chloride (saturated, 10 mL). The combined aqueous layers were extracted with ethyl acetate (10 mL) and the combined organic extracts dried over sodium sulfate. Filtration and concentration followed by purification by chromatography (silica, heptane:ethyl acetate 1:0 to 7:3) afforded the title compound (191 mg, 42%) as a colorless oil MS: m/e=325.3 [M+H]$^+$.

b) 6-(5-Methyl-3-phenyl-isoxazol-4-ylmethoxy)-nicotinic acid hydrazide

A mixture of 6-(5-methyl-3-phenyl-isoxazol-4-ylmethoxy)-nicotinic acid methyl ester (1.0 g, 3 mmol), hydrazine (3.09 g, 62 mmol) and ethanol (1 mL) was heated at 90° C. for 5 h. The mixture was cooled and concentrated to give a white residue that was triturated with chloroform and filtered. The filtrate was concentrated to afford the title compound (743 mg, 49%) as a white solid. MS: m/e=325.4 [M+H]$^+$.

EXAMPLE 2

6-((5-Methyl-3-phenyl-isoxazol-4-yl)-methoxy)-N-morpholin-4-yl-nicotinamide

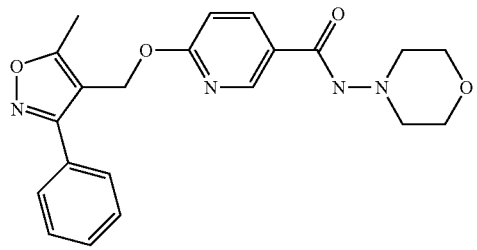

a) 6-(5-Methyl-3-phenyl-isoxazol-4-ylmethoxy)-nicotinic acid

To a solution of 6-(5-methyl-3-phenyl-isoxazol-4-yl-methoxy)-nicotinic acid methyl ester (3.89 g, 120 mmol) in ethanol (40 mL) was added aqueous sodium hydroxide (1 M, 36 mL, 36 mmol). The resulting mixture was heated under reflux for 2 h and then cooled to room temperature and concentrated. Addition of aqueous sodium hydroxide (1 M, 50 mL) was followed by washing with tert-butylmethylether (100 mL). The aqueous phase was acidified with aqueous hydrogen chloride (conc.) to pH=1 and extracted with tert-butylmethylether (100 mL). The organic layers was washed with water (50 mL) and aqueous sodium chloride (saturated, 50 mL). Drying over sodium sulfate and concentration afforded the title compound (1.68 g, 45%) as an off white solid. MS: m/e=309.3 [M−H]$^-$.

b) 6-(5-Methyl-3-phenyl-isoxazol-4-ylmethoxy)-N-morpholin-4-yl-nicotinamide To a stirred solution of 6-(5-methyl-3-phenyl-isoxazol-4-ylmethoxy)-nicotinic acid (100 mg, 0.32 mmol) in DMF (5 mL) at room temperature under argon was added N-amino-morpholine (36 mg, 0.35 mmol), 2-(1H-benzotriazole-1-yl)-1,1,3,3-tetramethyluronium tetrafluoroborate (0.114 g, 0.35 mmol) and N,N-diisopropylethylamine (208 mg, 1.6 mmol). After 15 h the reaction mixture was concentrated, diluted with water and extracted with ethyl acetate. The combined organic extracts were dried over sodium sulfate, filtered and concentrated. Purification by chromatography (silica, dichloromethane:methanol 1:0 to 97.5:2.5) afforded the title compound (50 mg, 40%) as a white solid. MS: m/e=395.1 [M+H]$^+$.

EXAMPLE 3

6-((5-Methyl-3-phenyl-isoxazol-4-yl)-methoxy)-N-piperidin-1-yl-nicotinamide

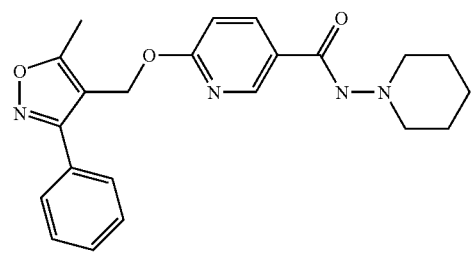

As described for example 2b, 6-(5-methyl-3-phenyl-isoxazol-4-ylmethoxy)-nicotinic acid (100 mg, 0.32 mmol) was converted, using N-aminopiperidine instead of N-aminomorpholine to the title compound (27 mg, 21%) which was obtained as a white solid. MS: m/e=393.2 [M+H]⁺.

EXAMPLE 4

6-((5-Methyl-3-phenyl-isoxazol-4-yl)-methoxy)-N-pyrrolidin-1-yl-nicotinamide

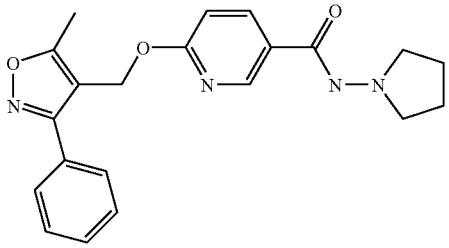

As described for example 2b, 6-(5-methyl-3-phenyl-isoxazol-4-ylmethoxy)-nicotinic acid (100 mg, 0.32 mmol) was converted, using N-aminopyrrolinne HCl instead of N-aminomorpholine to the title compound (80 mg, 66%) which was obtained as a white solid. MS: m/e=379.4 [M+H]⁺.

EXAMPLE 5

N-(1,1-Dioxo-1,6-thiomorpholin-4-yl)-6-((5-methyl-3-phenyl-isoxazol-4-yl)-methoxy)-nicotinamide

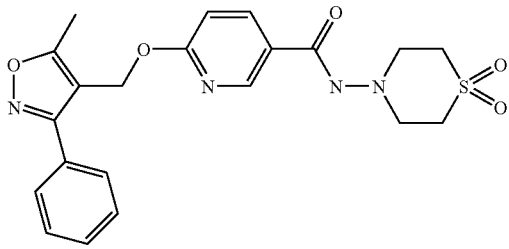

As described for example 2b, 6-(5-methyl-3-phenyl-isoxazol-4-ylmethoxy)-nicotinic acid (100 mg, 0.32 mmol) was converted, using N-aminothiomorpholine 1,1-dioxide instead of N-aminomorpholine to the title compound (95 mg, 67%) which was obtained as a white solid. MS: m/e=443.2 [M+H]⁺.

EXAMPLE 6

6-((5-Methyl-3-phenyl-isoxazol-4-yl)-methoxy)-nicotinic acid N'-(methyl sulfonyl)-hydrazide

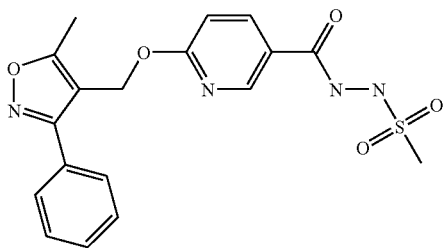

As described for example 2b, 6-(5-methyl-3-phenyl-isoxazol-4-ylmethoxy)-nicotinic acid (200 mg, 0.65 mmol) was converted, using methane sulfonyl hydrazide instead of N-aminomorpholine to the title compound (85 mg, 33%) which was obtained as a white solid. MS: m/e=401.0 [M–H]⁻.

EXAMPLE 7

6-[(3-(5-Fluoro-pyridin-2-yl)-5-methyl-isoxazol-4-yl)-methoxy]-N-morpholin-4-yl-nicotinamide

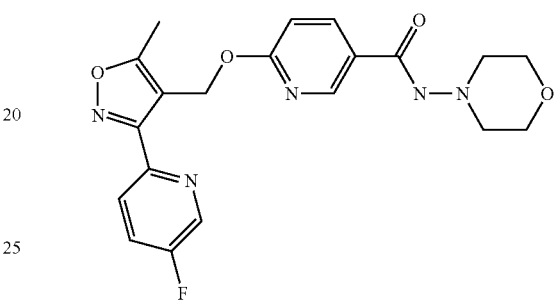

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]⁺.

b) 3-(5-Fluoro-pyridin-2-yl)-5-methyl-isoxazole-4-carboxylic acid ethyl ester

To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (SiO₂, heptane:ethyl acetate=100:0 to 20:80) afforded the title compound (5.83 g, 67%) as yellow oil. MS: m/e=251.1 [M+H]⁺.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (SiO$_2$, heptane:ethyl acetate=50:50 to 0:100) afforded the title compound (1.47 g, 71%) as a light yellow solid. MS: m/e=209.1 [M+H]$^+$.

d) 6-[3-(5-Fluoro-pyridin-2-yl)-5-methyl-isoxazol-4-ylmethoxy]-nicotinic acid methyl ester As described for example 1a, [3-(5-fluoro-pyridin-2-yl)-5-methyl-isoxazol-4-yl]-methanol (600 mg, 2.8 mmol) was converted, instead of (5-methyl-3-phenyl-isoxazol-4-yl)-methanol, to the title compound (210 mg, 21%) which was obtained as a white solid. MS: m/e=344.1 [M+H]$^-$.

e) 6-[3-(5-Fluoro-pyridin-2-yl)-5-methyl-isoxazol-4-ylmethoxy]-N-morpholin-4-yl-nicotinamide A solution of trimethylaluminium (2 M in toluene, 0.58 mL, 1.1 mmol) was added dropwise (exothermic) to a solution of N-aminomorpholine (111 µL, 1.2 mmol) in dioxane (2.5 mL) and the resulting mixture was stirred at room temperature for 1 h. Then a solution of 6-[3-(5-fluoro-pyridin-2-yl)-5-methyl-isoxazol-4-ylmethoxy]-nicotinic acid methyl ester (100 mg, 0.29 mmol) in dioxane (2.5 mL) was added. The resulting mixture was then heated at 90° C. overnight and then cooled to room temperature and then poured into Seignette salt solution and extracted with ethyl acetate which was then washed with brine, dried over sodium sulfate and evaporated. Purification by chromatography (silica, dichloromethane:methanol=9:1) afforded the title compound (47 mg, 40%) which was obtained as a white solid. MS: m/e=414.3 [M+H]$^+$.

EXAMPLE 8

6-((3-Butyl-5-methyl-isoxazol-4-yl)-methoxy)-N-morpholin-4-yl-nicotinamide

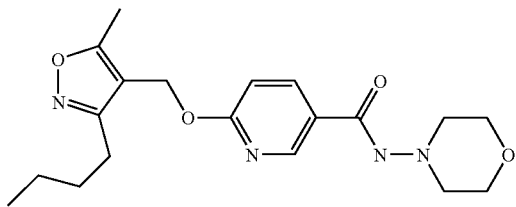

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl (E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, then the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]$^+$.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithium aluminium hydride (2.03 g, 53.4 mmol) in five portions. After 1 h the reaction mixture was quenched dropwise with Seignette salt solution. The reaction mixture was filtered and the filtrate extracted with ethyl acetate. The combined organic extracts were washed with Seignette salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]$^+$.

c) 6-(3-Butyl-5-methyl-isoxazol-4-ylmethoxy)-nicotinic acid methyl ester

As described for example 1a, (3-butyl-5-methyl-isoxazol-4-yl)-methanol (1.0 g, 5.9 mmol) was converted, instead of (5-methyl-3-phenyl-isoxazol-4-yl)-methanol, to the title compound (905 mg, 45%) which was obtained as a light yellow oil. MS: m/e=305.3 [M+H]$^+$.

d) 6-(3-Butyl-5-methyl-isoxazol-4-ylmethoxy)-N-morpholin-4-yl-nicotinamide

As described for example 7e, 6-(3-butyl-5-methyl-isoxazol-4-ylmethoxy)-nicotinic acid methyl ester (200 mg, 0.66 mmol) was converted, instead of 6-[3-(5-fluoro-pyridin-2-yl)-5-methyl-isoxazol-4-ylmethoxy]-nicotinic acid methyl ester, to the title compound (120 mg, 49%) which was obtained as a white solid. MS: m/e=375.3 [M+H]$^+$.

EXAMPLE 9

6-((3-Butyl-5-methyl-isoxazol-4-yl)-methoxy)-N-pyrrolidin-1-yl-nicotinamide

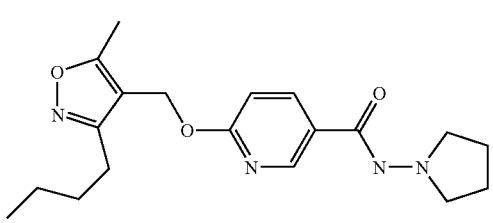

As described for example 8d, 6-(3-butyl-5-methyl-isoxazol-4-ylmethoxy)-nicotinic acid methyl ester (200 mg, 0.66 mmol) was converted, using N-aminopyrrolidine instead of N-aminomorpholine, to the title compound (40 mg, 17%) which was obtained as an off white solid. MS: m/e=359.2 [M+H]$^+$.

EXAMPLE 10

6-((3-Butyl-5-methyl-isoxazol-4-yl)-methoxy)-nicotinic acid 2,2-dimethyl-hydrazide

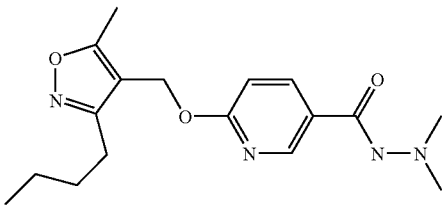

a) 6-(3-Butyl-5-methyl-isoxazol-4-ylmethoxy)-nicotinic acid

To a suspension of 6-(3-butyl-5-methyl-isoxazol-4-ylmethoxy)-nicotinic acid methyl ester (1.0 g, 3.3 mmol) in THF (6 mL) was added a solution of lithium hydroxide monohydrate (248 mg, 9.8 mmol) in water (6 mL) added and the resulting mixture stirred at room temperture for 5 h. The mixture was acidified to pH 4 with HCl (1 N, 4.5 mL) and the resulting mixture extracted with ethyl acetate. The combined organic layers were then washed with water and brine, dried over sodium sulfate and evaporated. Purification by chromatography (silica, heptane:ethyl acetate=1:0 to 0:1) afforded the title compound (654 mg, 76%) which was obtained as a white solid. MS: m/e=291.2 [M+H]+.

b) 6-(3-Butyl-5-methyl-isoxazol-4-ylmethoxy)-nicotinic acid N',N'-dimethyl-hydrazide To a stirred solution of 6-(3-butyl-5-methyl-isoxazol-4-ylmethoxy)-nicotinic acid (100 mg, 0.34 mmol) in DMF (5 mL) at room temperature under argon was added N,N-dimethylhydrazine (23 mg, 0.38 mmol), 2-(1H-benzotriazole-1-yl)-1,1,3,3-tetramethyluronium tetrafluoroborate (122 mg, 0.38 mmol) and N,N-diisopropylethylamine (223 mg, 1.7 mmol). After 15 h the reaction mixture was concentrated, diluted with water and extracted with ethyl acetate. The combined organic extracts were dried over sodium sulfate, filtered and concentrated. Purification by chromatography (silica, dichloromethane:methanol 1:0 to 97.5:2.5) afforded the title compound (38 mg, 33%) as a colourless gum. MS: m/e=333.3 [M+H]+.

EXAMPLE 11

6-((5-Methyl-3-phenyl-isoxazol-4-yl)-methoxy)-pyridazine-3-carboxylic acid morpholin-4-ylamide

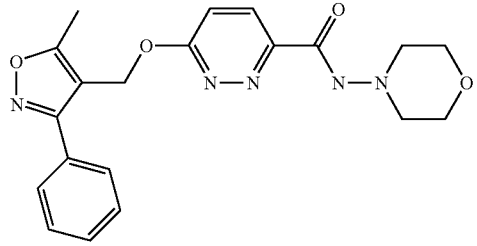

a) 3-Chloro-6-(5-methyl-3-phenyl-isoxazol-4-ylmethoxy)-pyridazine

To a solution of (5-methyl-3-phenyl-isoxazol-4-yl)-methanol (5.0 g, 26.4 mmol) in THF (50 mL) was added sodium hydride (55% dispersion in mineral oil, 1.27 g, 29.1 mmol). The mixture was stirred at room temperature for 30 min. After addition of 3,6-dichloropyridazine (4.33 g, 29.1 mmol) the mixture was stirred at room temperature for another 5 h. Then the mixture was evaporated, extracted (ethyl acetate/water) and the organic phase was dried with sodium sulfate and concentrated. Chromatography (SiO2, heptane:ethyl acetate=100:0 to 70:30) afforded the title compound (6.62 g, 83%) as a white solid. MS: m/e=302.0 [M+H]+.

b) 6-(5-Methyl-3-phenyl-isoxazol-4-ylmethoxy)-pyridazine-3-carboxylic acid methyl ester To a solution of 3-chloro-6-(5-methyl-3-phenyl-isoxazol-4-ylmethoxy)-pyridazine (2.0 g, 6.6 mmol) in methanol (80 mL) was added sodium carbonate (710 mg, 6.6 mmol), 1,1'-bis(diphenylphosphino)ferrocene (367 mg, 0.6 mmol) and palladium(II) acetate (149 mg, 0.6 mmol). The resulting mixture was stirred at 50° C. overnight under a carbon monoxide atmosphere. After cooling to room temperature it was filtered through Celite® and concentrated. Purification by chromatography (silica, dichloromethane:methanol 1:0 to 9:1) afforded the title compound (960 mg, 40%) as a light brown solid. MS: m/e=326.3 [M+H]+.

c) 6-(5-Methyl-3-phenyl-isoxazol-4-ylmethoxy)-pyridazine-3-carboxylic acid

As described for example 10a, 6-(5-methyl-3-phenyl-isoxazol-4-ylmethoxy)-pyridazine-3-carboxylic acid methyl ester (960 mg, 2.95 mmol) was converted, instead of 6-(3-butyl-5-methyl-isoxazol-4-ylmethoxy)-nicotinic acid methyl ester, to the title compound (415 mg, 45%) which was obtained as a white solid. MS: m/e=310.1 [M−H]−.

d) 6-(5-Methyl-3-phenyl-isoxazol-4-ylmethoxy)-pyridazine-3-carboxylic acid morpholin-4-ylamide To a stirred solution of 6-(5-methyl-3-phenyl-isoxazol-4-ylmethoxy)-pyridazine-3-carboxylic acid (215 mg, 0.69 mmol) in DMF (5 mL) at room temperature under argon was added N-aminomorpholine (78 mg, 0.76 mmol), 2-(1H-benzotriazole-1-yl)-1,1,3,3-tetramethyluronium tetrafluoroborate (244 mg, 0.76 mmol) and N,N-diisopropylethylamine (446 mg, 3.4 mmol). After 15 h the reaction mixture was concentrated, diluted with water and extracted with ethyl acetate. The combined organic extracts were dried over sodium sulfate, filtered and concentrated. Purification by chromatography (silica, dichloromethane:methanol 1:0 to 97.5:2.5) afforded the title compound (101 mg, 37%) as a white gum. MS: m/e=396.1 [M+H]+.

The invention claimed is:
1. A compound of formula I

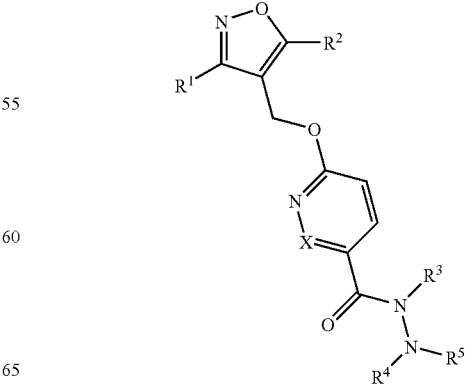

wherein

X is CR⁶ or N, wherein R⁶ is hydrogen or lower-alkyl;

R¹ is lower-alkyl, aryl or heteroaryl,
   wherein lower-alkyl is optionally substituted with 1-4 substituents independently selected from the group consisting of halogen, cyano, hydroxy and lower-alkoxy, and wherein aryl and heteroaryl are each optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—NH₂, lower-alkyl-CO—N(H,lower-alkyl), lower-alkyl-CO—N(lower-alkyl)₂, lower-alkyl-NH₂, lower-alkyl-N(H,lower-alkyl), lower-alkyl-N(lower-alkyl)₂, lower-alkoxy-lower-alkyl, CO-lower-alkyl, COOH, COO-lower-alkyl, CONH₂, CON(H,lower-alkyl), CON(lower-alkyl)₂, cycloalkyl, heterocyclyl, aryl, heteroaryl, NH₂, N(H, lower-alkyl), N(lower-alkyl)₂, hydroxy, lower-alkoxy, phenyloxy, SO₂-lower-alkyl, SO₂—NH₂, SO₂—N(H,lower-alkyl) and SO₂—N(lower-alkyl)₂;

R² is hydrogen or lower-alkyl which is optionally substituted with 1-4 substituents independently selected from the group consisting of halogen, cyano, lower-alkyl and lower-alkoxy;

R³ is hydrogen or lower-alkyl which is optionally substituted with 1-4 substituents independently selected from the group consisting of halogen, cyano, hydroxy, lower-alkyl and lower-alkoxy;

R⁴ and R⁵ are each independently selected from the group consisting of hydrogen, lower-alkyl, SO₂-lower-alkyl, cycloalkyl and heterocyclyl, optionally substituted with 1-4 substituents independently selected from the group consisting of halogen, cyano, hydroxy, lower-alkyl and lower-alkoxy,
   or wherein R⁴ and R⁵, together with the nitrogen atom to which they are attached, form a heterocyclyl, optionally substituted with 1-4 substituents independently selected from the group consisting of halogen, cyano, hydroxy, oxo, lower-alkyl and lower-alkoxy; with the proviso that R⁴ and R⁵ are not both H;

or a pharmaceutically acceptable salt or ester thereof.

2. The compound of claim 1, wherein X is CH.

3. The compound of claim 1, wherein R¹ is lower-alkyl, aryl or heteroaryl substituted with halogen.

4. The compound of claim 3, wherein R¹ is n-butyl, phenyl or 5-fluoro-pyridin-2-yl.

5. The compound of claim 4, wherein R¹ is phenyl or 5-fluoro-pyridin-2-yl.

6. The compound of claim 1, wherein R² is lower-alkyl.

7. The compound of claim 6, wherein R² is methyl.

8. The compound of claim 1, wherein R³ is hydrogen.

9. The compound of claim 1, wherein R⁴ and R⁵ are each independently selected from the group consisting of hydrogen, lower-alkyl and SO₂-lower-alkyl with the proviso that R⁴ and R⁵ are not both hydrogen.

10. The compound of claim 9, wherein R⁴ and R⁵ are each independently selected from the group consisting of hydrogen, methyl and SO₂-methyl with the proviso that R⁴ and R⁵ are not both hydrogen.

11. The compound of claim 10, wherein R⁴ is hydrogen and R⁵ is SO₂-methyl.

12. The compound of claim 9, wherein both R⁴ and R⁵ are both methyl.

13. The compound of claim 1, wherein R⁴ and R⁵, together with the nitrogen atom to which they are attached, form a heterocyclyl.

14. The compound of claim 13, wherein R⁴ and R⁵, together with the nitrogen atom to which they are attached, form a heterocyclyl selected from the group consisting of morpholin-4-yl, piperidin-1-yl, pyrrolidin-1-yl and 1,1-di-oxo-thiomorpholin-4-yl.

15. The compound of claim 14, wherein R⁴ and R⁵, together with the nitrogen atom to which they are attached, form a heterocyclyl selected from the group of morpholin-4-yl, pyrrolidin-1-yl and 1,1-dioxo-thiomorpholin-4-yl.

16. The compound of claim 1 selected from the group consisting of:
   6-((5-Methyl-3-phenyl-isoxazol-4-yl)-methoxy)-N-morpholin-4-yl-nicotinamide,
   6-((5-Methyl-3-phenyl-isoxazol-4-yl)-methoxy)-N-piperidin-1-yl-nicotinamide,
   6-((5-Methyl-3-phenyl-isoxazol-4-yl)-methoxy)-N-pyrrolidin-1-yl-nicotinamide,
   N-(1,1-Dioxo-1,6-thiomorpholin-4-yl)-6-((5-methyl-3-phenyl-isoxazol-4-yl)-methoxy)-nicotinamide,
   6-((5-Methyl-3-phenyl-isoxazol-4-yl)-methoxy)-nicotinic acid N'-(methyl sulfonyl)-hydrazide,
   6-[(3-(5-Fluoro-pyridin-2-yl)-5-methyl-isoxazol-4-yl)-methoxy]-N-morpholin-4-yl-nicotinamide,
   6-((3-Butyl-5-methyl-isoxazol-4-yl)-methoxy)-N-morpholin-4-yl-nicotinamide,
   6-((3-Butyl-5-methyl-isoxazol-4-yl)-methoxy)-N-pyrrolidin-1-yl-nicotinamide,
   6-((3-Butyl-5-methyl-isoxazol-4-yl)-methoxy)-nicotinic acid 2,2-dimethyl-hydrazide, and
   6-((5-Methyl-3-phenyl-isoxazol-4-yl)-methoxy)-pyridazine-3-carboxylic acid morpholin-4-ylamide,
or a pharmaceutically acceptable salt or ester thereof.

17. The compound of claim 16, selected from the group consisting of:
   6-((5-Methyl-3-phenyl-isoxazol-4-yl)-methoxy)-N-morpholin-4-yl-nicotinamide,
   6-((5-Methyl-3-phenyl-isoxazol-4-yl)-methoxy)-N-pyrrolidin-1-yl-nicotinamide,
   N-(1,1-Dioxo-1,6-thiomorpholin-4-yl)-6-((5-methyl-3-phenyl-isoxazol-4-yl)-methoxy)-nicotinamide, and
   6-[(3-(5-Fluoro-pyridin-2-yl)-5-methyl-isoxazol-4-yl)-methoxy]-N-morpholin-4-yl-nicotinamide,
or a pharmaceutically acceptable salt or ester thereof.

18. A pharmaceutical composition comprising a a therapeutically effective amount of a compound of formula I

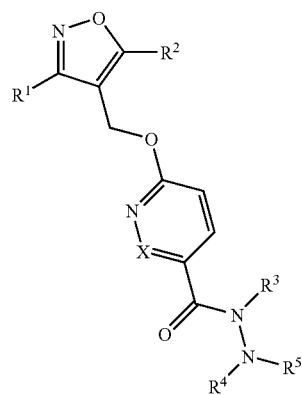

wherein

X is $CR^6$ or N, wherein $R^6$ is hydrogen or lower-alkyl;

$R^1$ is lower-alkyl, aryl or heteroaryl, wherein lower-alkyl is optionally substituted with 1-4 substituents independently selected from the group consisting of halogen, cyano, hydroxy and lower-alkoxy, and wherein aryl and heteroaryl are each optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H,lower-alkyl), lower-alkyl-CO—N(lower-alkyl)$_2$, lower-alkyl-$NH_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$-$NH_2$, $SO_2$—N(H,lower-alkyl) and $SO_2$—N(lower-alkyl)$_2$;

$R^2$ is hydrogen or lower-alkyl which is optionally substituted with 1-4 substituents independently selected from the group consisting of halogen, cyano, lower-alkyl and lower-alkoxy;

$R^3$ is hydrogen or lower-alkyl which is optionally substituted with 1-4 substituents independently selected from the group consisting of halogen, cyano, hydroxy, lower-alkyl and lower-alkoxy;

$R^4$ and $R^5$ are each independently selected from the group consisting of hydrogen, lower-alkyl, $SO_2$-lower-alkyl, cycloalkyl and heterocyclyl, optionally substituted with 1-4 substituents independently selected from the group consisting of halogen, cyano, hydroxy, lower-alkyl and lower-alkoxy, or wherein $R^4$ and $R^5$, together with the nitrogen atom to which they are attached, form a heterocyclyl, optionally substituted with 1-4 substituents independently selected from the group consisting of halogen, cyano, hydroxy, oxo, lower-alkyl and lower-alkoxy; with the proviso that $R^4$ and $R^5$ are not both hydrogen;

or a pharmaceutically acceptable salt or ester thereof and a pharmaceutically acceptable carrier.

* * * * *